United States Patent [19]

Grevious et al.

[11] Patent Number: 5,127,401
[45] Date of Patent: Jul. 7, 1992

[54] METHOD OF AND APPARATUS FOR MULTI-VECTOR PACING ARTIFACT DETECTION

[75] Inventors: John Grevious, Minneapolis; Scott Armitage, Golden Valley, both of Minn.

[73] Assignee: Medtronic, Inc., Minneapolis, Minn.

[21] Appl. No.: 611,901

[22] Filed: Nov. 9, 1990

[51] Int. Cl.$^5$ .............................................. A61N 1/37
[52] U.S. Cl. ............................................. 128/419 PT
[58] Field of Search ................... 128/696, 697, 419 PT

[56] References Cited

U.S. PATENT DOCUMENTS

| | | | |
|---|---|---|---|
| 3,871,363 | 3/1975 | Day | 128/419 PT |
| 3,923,041 | 12/1975 | Stasz et al. | 128/697 |
| 4,023,865 | 5/1977 | Ohlsson | 128/696 |
| 4,121,576 | 10/1978 | Greensite | 128/698 |
| 4,136,690 | 1/1979 | Anderson et al. | 128/698 |
| 4,170,227 | 10/1979 | Feldman et al. | 128/696 |
| 4,216,780 | 8/1980 | Rubel et al. | 128/698 |
| 4,226,245 | 10/1980 | Bennett, Jr. | 128/419 PT |
| 4,263,919 | 4/1981 | Levin | 128/708 |
| 4,527,567 | 7/1985 | Fischler et al. | 128/419 PT |
| 4,593,702 | 6/1986 | Kepski et al. | 128/696 |

FOREIGN PATENT DOCUMENTS 0086429 2/1983 European Pat. Off. .

OTHER PUBLICATIONS

"Rhythm Analysis Using Vector Cardiograms", by Murthy et al., IEEE Transactions on Biomedical Engineering, vol. BME-32, No. 2, Feb. '85.

Primary Examiner—William E. Kamm
Attorney, Agent, or Firm—John A. Rissman; Harold R. Patton

[57] ABSTRACT

A technique for improving detection of the pacing artifact in patients having artificially paced myocardial contractions. The improved detection is accomplished by sensing all three commonly monitored EKG leads. Each lead is differentially amplified and rectified to produce a signal of absolute value. The resulting three signals are algebraically summed and differentiated. Because the pacing artifact consists of higher frequency components than the naturally occurring QRS complex, it can easily be detected by its much larger first derivative.

Reliable detection of the artificial pacing artifact is extremely important in monitoring and programming implantable pacers. It is necessary to accurately determine whether a pacing pulse has been delivered and precisely measure the time of its occurrence.

8 Claims, 5 Drawing Sheets

METHOD OF AND APPARATUS FOR MULTI-VECTOR PACING ARTIFACT DETECTION

CROSS REFERENCE TO CO-PENDING APPLICATIONS

None.

BACKGROUND OF THE INVENTION

1. Field of the Invention

The present invention generally relates to medical monitoring devices, and more particularly, relates to medical devices used to detect artifacts produced by artificial cardiac pacing.

2. Description of the Prior Art

It is known in the art to monitor electrical activity of the human heart for diagnostic and related medical purposes. Such monitoring is also important for determining proper operation of and for permitting programming of implanted cardiac pacers. Medtronic ® Model 5311 pacing system programmer is a state of the art device used for such an application. At times, however, the signal-to-noise ratio of such systems becomes too low to adequately identify the relatively high frequency pacing artifact.

U.S. Pat. No. 4,023,565 issued to Ohlsson describes circuitry for recording EKG signals from multiple lead inputs. Similarly, U.S. Pat. No. 4,263,919 issued to Levin; U.S. Pat. No. 4,170,227 issued to Feldman et al.; and U.S. Pat. No. 4,593,702 issued to Kepski et al., describe multiple electrode systems which combine signals for artifact rejection.

The primary use for multiple electrode systems in the prior art appears to be vectorcardiography. This is a technique whereby the direction of depolarization of the heart is monitored, as well as the amplitude. U.S. Pat. No. 4,121,576 issued to Greensite discusses such a system.

U.S. Pat. No. 4,136,690 issued to Anderson et al., shows a vectorcardiographic system used for arrhythmia analysis. Similar techniques are described in "Rhythm Analysis Using Vectorcardiograms", *Transactions on Biomedical Engineering*, Volume BME-32 No. 2, February 1985, by Reddy, Murthy and Chatterjee. European Patent 0 086 429 issued to Sanz and U.S. Pat. No. 4,216.780 issued to Rubel et al., also discuss vectorcardiography and related systems.

SUMMARY OF THE INVENTION

The present invention overcomes the disadvantages of the prior art systems by providing a method of and apparatus for monitoring expressly directed to allow a maximized detection threshold level thereby improving the signal-to-noise ratio of pacing artifact detection. This is accomplished by using inputs from the three standard EKG leads. Unlike prior art systems, however, the pacing artifact is not rejected even though it is above the passband of the EKG signal.

The three standard lead inputs are each amplified and differentiated. The resulting three signals are then rectified to produce absolute valued results prior to being summed. The summation of the three signals yields a relatively high signal level that is easily detected. The present invention eliminates the need for lowering the detection threshold to compensate for poor artifact/sensing vector alignment common for conventional systems.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
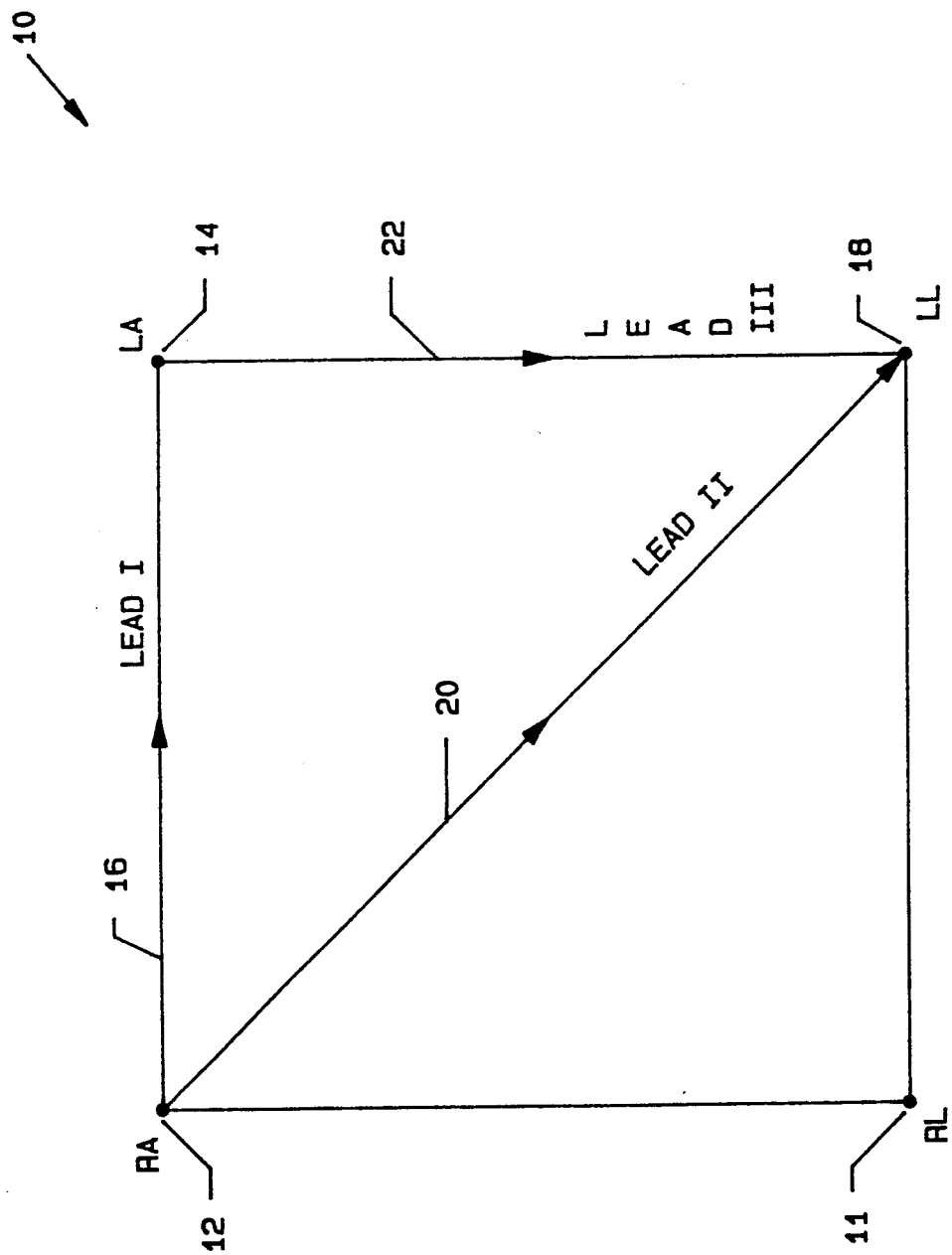
FIG. 1 is a graphical representation of the directional components of the three common EKG leads.

FIG. is a graphical representation 10 of the directional relationships of the three most common EKG leads. Lead I, shown as vector 16, is measured between right arm 12 and left arm 14. This is often the lead of choice for simple monitoring, as it tends to be the most easily implemented.

Lead II is represented by vector 20. It is measured between right arm 12 and left leg 18. Vector 22 represents Lead III. It is measured from left arm 14 to left leg 18. Right leg 11 is not used for these three leads.

Maximum amplitude is sensed whenever the depolarization signal (and pacing artifact) occurs parallel to the vector of a given lead. Therefore, the use of all three leads optimizes the probability that the sensed signal will be of acceptable amplitude for monitoring purposes. However, because these three leads tend to be within a single plane which is parallel to the front of the patient's body, it may yet be difficult to monitor signals which are essentially normal to this plane. Though it would be possible to prevent this using other than the three most common leads (e.g. measure between electrodes located at the front and back of the patient), the additional effort is probably not justified.

Figure 2:
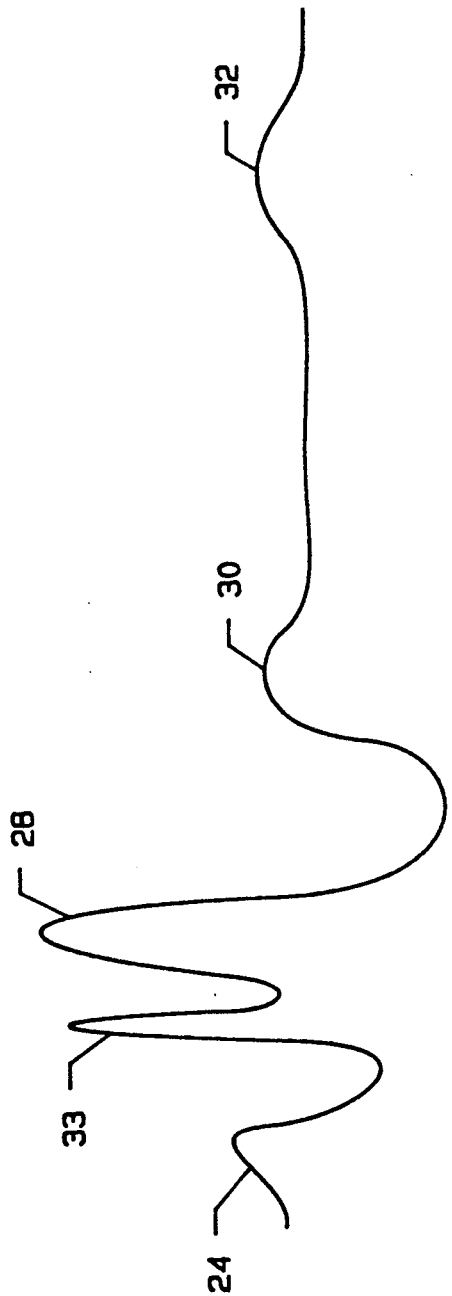
FIG. 2 is a graphical representation of an EKG signal containing a pacing artifact.

FIG. 2 is a graphical representation of an observed EKG signal containing a pacing artifact 33. The most distinguishing feature is "R" wave 28 representing the electrical depolarization of the ventricles. "Q" wave 24 shows the atrial depolarization, and "S" and "T" waves 30 and 32 are associated with repolarization.

It is important to note that pacing artifact 33 is ordinarily sensed as a lower amplitude and composed of much higher frequency components than "R" wave 28. This tends to make pacing artifact 33 difficult to monitor using ordinary EKG equipment.

Figure 3:
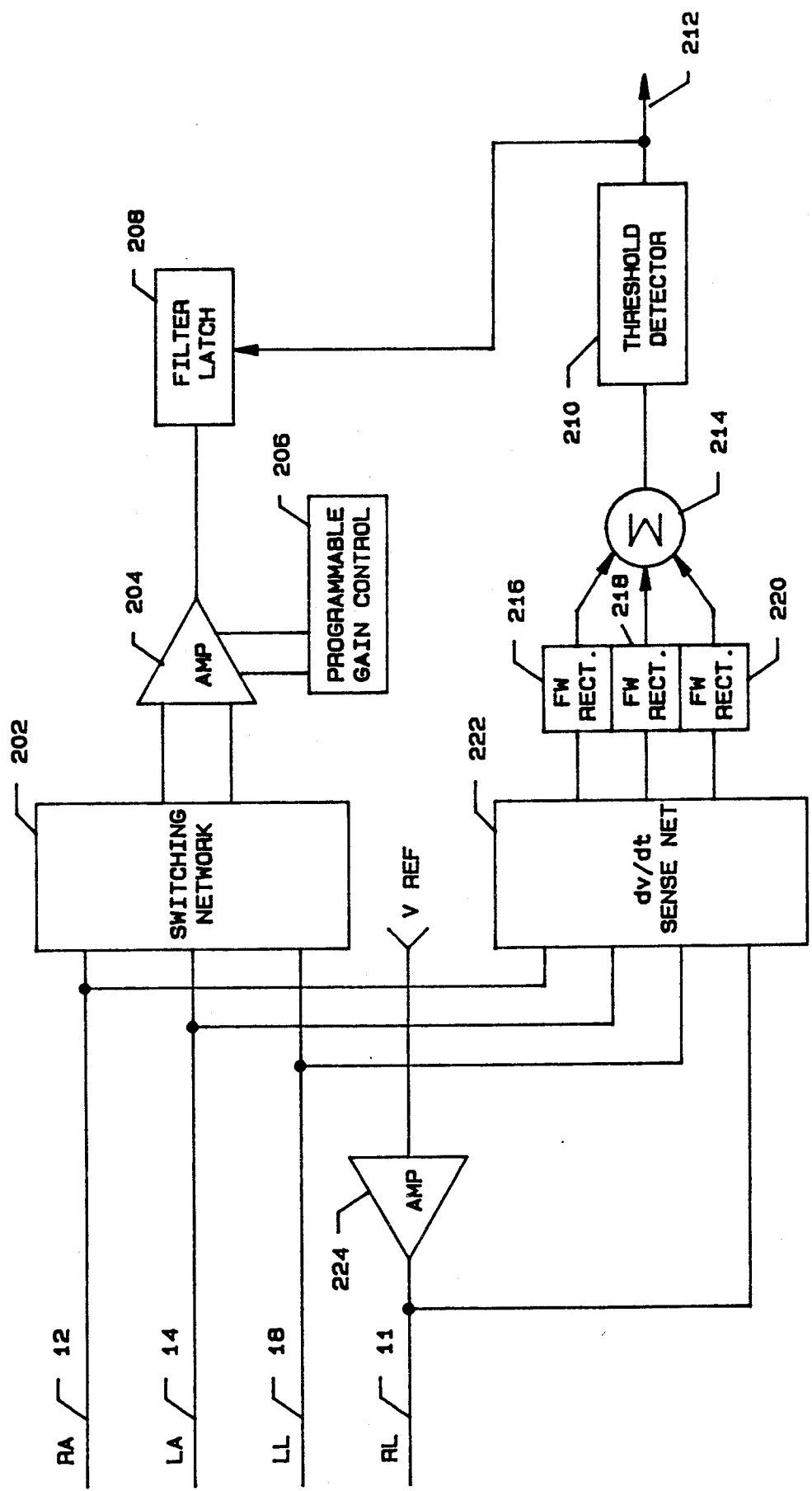
FIG. 3 is a functional representation of the operation of the present invention; and, FIG. 4A and FIG. 4B are an electrical block diagram of a circuit employing the present invention.

FIG. 3 is a functional diagram for a circuit employing the present invention. Right arm 12, left arm 14, left leg 18, and right leg 11 are coupled as inputs to the circuit as shown. The connection to right leg 11 functions only as a reference point as shown. The reference voltage is established by amplifier 224.

Switching network 202 serves to select from among the various leads to provide a single monitoring or recording output. The selection is ordinarily accomplished manually by the attending medical personnel. Amplifier 204 amplifies the selected signal with the output amplitude controlled by programmable gain control 206 to conveniently fit within the modulus of the monitoring and/or recording system. Final filtering is accomplished in accordance with filter latch 208.

Pacing artifact detection is accomplished by differentiation, rectification, algebraic addition, and thresholding of the three signals from the individual leads. Differentiation may be accomplished either before or after addition. For the purposes of this illustration and not to be viewed as limiting of the present invention, differentiation is shown as occurring first. This is done by sense network 222. In practice, &his tends to be a complex function which may be more efficiently accomplished after the algebraic addition step as shown in the preferred embodiment (see also FIG. 4A and FIG. 4B).

The three derivatives of the lead signals are rectified by full wave rectifiers 216, 218, and 220, respectively. Rectification must be accomplished before algebraic addition, because the polarity of one or more of the signals may be inverted. If the algebraic addition step were performed without full wave rectification, the signals may tend to cancel rather than be additive to one another.

Summer 214 performs algebraic addition of the three full wave rectified signals. The output of summer 214 is supplied to threshold detector 210. To be even more effective, thresholding may be accomplished within the anticipated pass band of the pacing artifact using a band pass filter internal to threshold detector 210. The output of threshold detector 210 is a binary indication of a sensed pacing artifact. It is provided as output 212 and is also used to trigger filter latch 208.

Figure 4A:
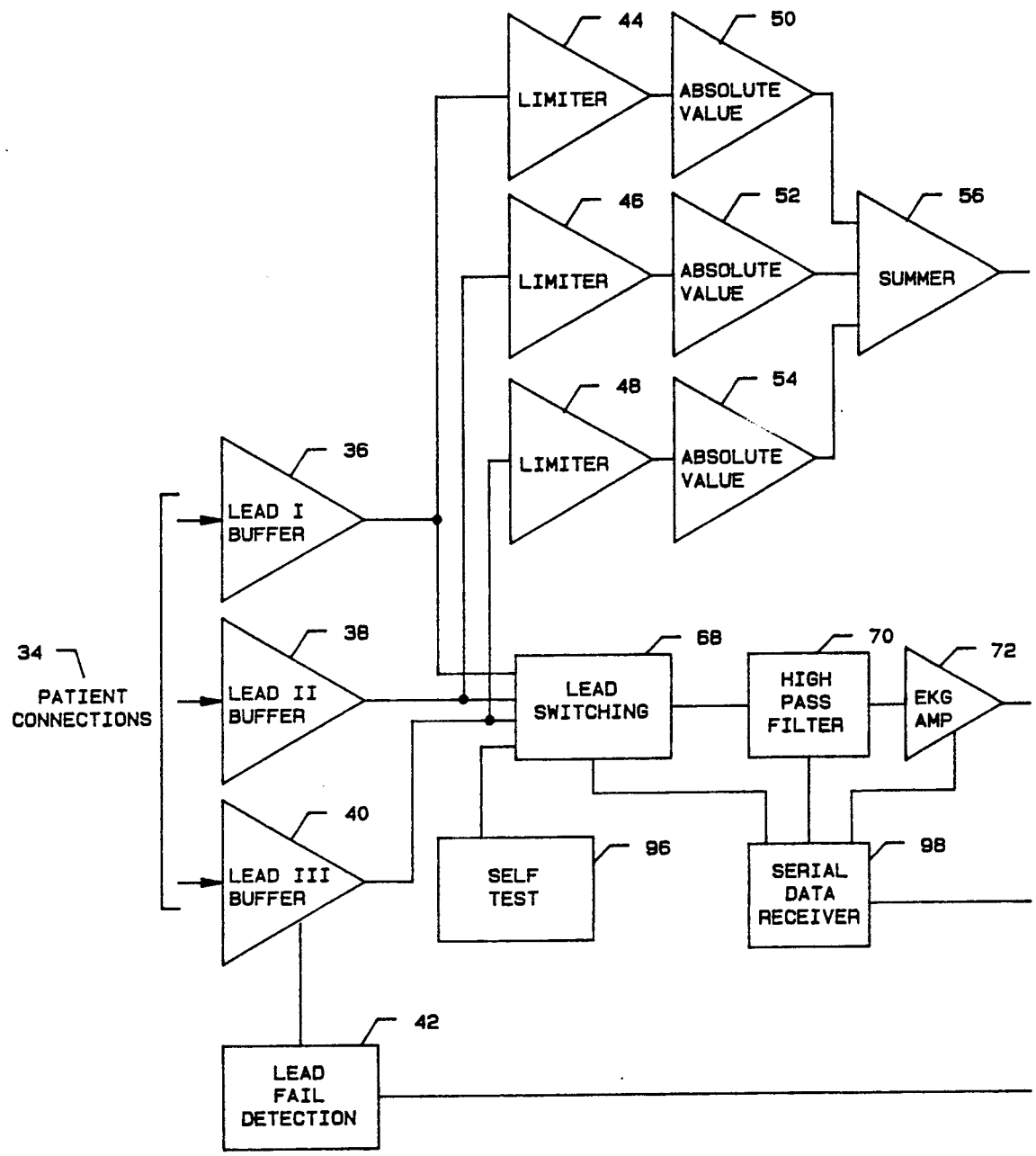
Figure 4B:
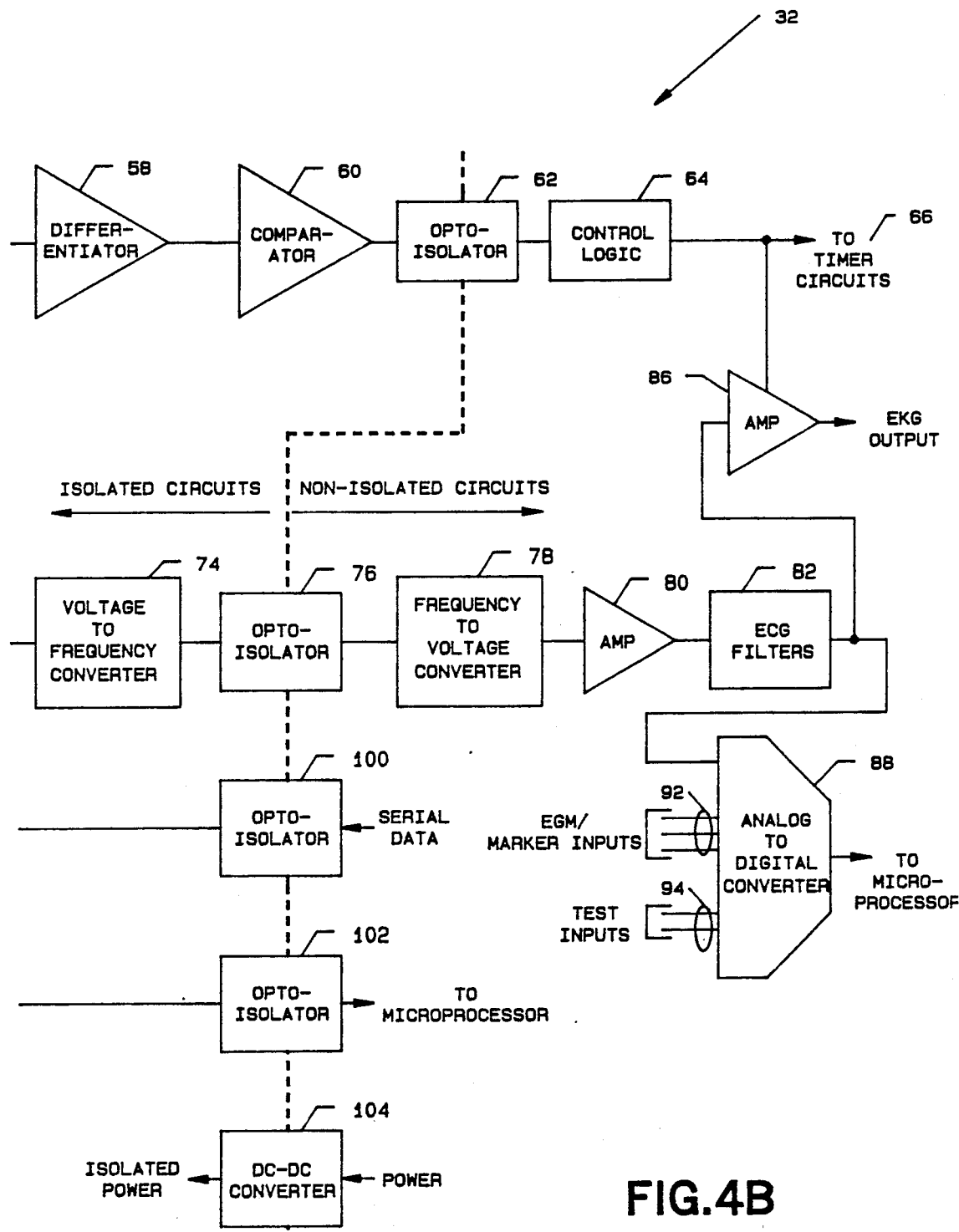

FIG. 4A and FIG. 4B, are a block diagram of the electrical circuitry of the preferred embodiment of the present invention. Patient connections 34 are coupled to Lead I Buffer 36, Lead II Buffer 38, and Lead III Buffer 40, wherein each lead signal is differentially amplified and pass band filtered. Lead switching 68 selects between leads based upon serial data receiver 98. High pass filter 70 filters the selected signal which is amplified by EKG amplifier 72.

Voltage to frequency converter 74 converts the signal which is isolated by opto-isolator 76. This isolation is a safety consideration to ensure that any leakage currents used in the remainder of the circuitry are not transferred via failure or otherwise to the patient.

Integration is performed by frequency to voltage converter 78. The resulting EKG signal is amplified by amp 80 and filtered by filter 82. The resulting signal is digitized by analog to digital converter 88 and supplied to a microprocessor (not shown). Analog to digital converter 88 accepts test inputs 94 and EGM/marker inputs for digitization as well. The analog EKG signal is supplied to amplifier 86 for use in the analog domain. Additional processing of the digitized EKG signal may be accomplished in accordance with standard practice in the art.

Serial data receiver 98 receives serialized commands from the microprocessor for control of lead switching 68, high pass filter 70, and amplifier 72. The serial data stream is electrically isolated by opto-isolator !00 in accordance with the considerations described above.

Lead fail detection 42 monitors for malfunctions in the electrode/patient interface. Opto-isolator 102 provides the isolation for the failure data. Converter 104 ensures that the isolated circuitry is safely powered.

Detection of the pacing artifact is accomplished by supplying the three buffered lead signals to limiters 44, 46, and 48. These circuits clip the corresponding pacing artifact signals. Each signal is rectified by absolute value 50, 52, and 54. The signals are algebraically added by summer 56.

As explained above, it may be more practical to differentiate the one resultant signal following algebraic addition. This derivative is produced by differentiator 58. Comparator 60 compares the derivative to a voltage reference to obtain a binary indication of the presence of a pacing artifact. Opto-isolator 62 provides patient protection as discussed above.

Control logic 64 further processes the binary signal to permit control of timer circuits 66 and the addition of a pulse to amplifier 86 to mark the pacing artifact within the EKG output. The pacing artifact signal has thus been converted from an analog signal to a binary signal modulated in time. This signal is further used to monitor and control operation of the implanted cardiac pacing generator in the manner known in the art.

Having thus described the preferred embodiment of the present invention, those of skill in the art will be readily able to appreciate that the teachings found herein may be applied to yet other embodiments within the scope of the claims hereto attached.

We claim:

1. An apparatus for detecting a pacing artifact within an EKG signal, comprising:
    a. means for sensing a signal from each a plurality of EKG leads;
    b. means coupled to said sensing means for producing a composite signal from said plurality of EKG leads, said producing means further comprising means for algebraically adding each of said sensed signal from said plurality of EKG leads; and
    c. means coupled to said algebraic adding means for detecting said pacing artifact present within said composite signal.

2. An apparatus according to claim 1 wherein said algebraic adding means further comprises a full wave rectifier for obtaining the absolute value of each of said plurality of signals before said algebraic adding.

3. An apparatus according to claim 2 wherein said detecting means further comprises a differentiator whereby said detecting means detects said pacing artifact from a signal representing a derivative of said pacing artifact.

4. An apparatus according to claim 3 wherein said detecting means further comprises a comparator for comparing said derivative of said pacing artifact to a reference signal.

5. An apparatus according to claim 4 wherein said plurality of EKG leads further comprises Lead I, Lead II, and Lead III.

6. A method of detecting a pacing artifact within an EKG signal, comprising the steps of:
    a. sensing a plurality of signals wherein each of said plurality of signals represents a different one of a plurality of EKG leads;
    b. producing a composite signal from said plurality of signals, said step of producing comprising algebraically adding said plurality of signals; and
    c. detecting said pacing artifact within said composite signal.

7. A method according to claim 6 wherein said detecting further comprises:
    a. differentiating said composite signal;
    b. comparing said differentiated composite signal to a reference signal; and
    c. assuming said pacing artifact is present if said comparing shows that said differentiated composite signal is greater than said reference signal.

8. A method according to claim 6, further comprising the step of rectifying each of said plurality of signals before said step of producing.

* * * * *